United States Patent
Hasse

(10) Patent No.: US 11,304,931 B1
(45) Date of Patent: Apr. 19, 2022

(54) METHOD OF TREATING SUBJECT EXPOSED TO RADIATION IN SPACE

(71) Applicant: Adam M. Hasse, Driftwood, TX (US)

(72) Inventor: Adam M. Hasse, Driftwood, TX (US)

(*) Notice: Subject to any disclaimer, the term of this patent is extended or adjusted under 35 U.S.C. 154(b) by 211 days.

(21) Appl. No.: 16/164,019

(22) Filed: Oct. 18, 2018

Related U.S. Application Data

(60) Provisional application No. 62/584,971, filed on Nov. 13, 2017.

(51) Int. Cl.
*A61K 31/00* (2006.01)
*A61K 31/409* (2006.01)
*A61N 5/06* (2006.01)

(52) U.S. Cl.
CPC .............. *A61K 31/409* (2013.01); *A61N 5/06* (2013.01); *A61N 2005/0653* (2013.01); *A61N 2005/0654* (2013.01); *A61N 2005/0661* (2013.01); *A61N 2005/0667* (2013.01)

(58) Field of Classification Search
CPC ................... A61K 31/409; A61N 5/06; A61N 2005/0653; A61N 2005/0654; A61N 2005/0661; A61N 2005/0667
See application file for complete search history.

(56) References Cited

U.S. PATENT DOCUMENTS

| | | | |
|---|---|---|---|
| 4,976,960 A | 12/1990 | Grossman et al. | |
| 5,916,912 A | 6/1999 | Ames et al. | |
| 5,948,823 A | 9/1999 | Ben-Amotz et al. | |
| 6,254,898 B1 | 7/2001 | Bragaglia | |
| 6,787,147 B1 | 9/2004 | Huner et al. | |
| 7,435,725 B2 * | 10/2008 | Rosenbloom .......... | A61K 8/922 514/167 |
| 7,449,451 B2 | 11/2008 | Prasad et al. | |
| 2003/0103954 A1 | 6/2003 | Rosenbloom | |
| 2006/0212025 A1 * | 9/2006 | McDaniel ............ | A61N 5/0617 606/9 |
| 2008/0138393 A1 | 6/2008 | Leverett et al. | |
| 2013/0224281 A1 | 8/2013 | Montesinos et al. | |
| 2014/0023701 A1 | 1/2014 | Montesinos et al. | |

OTHER PUBLICATIONS

Askew, "Work at high altitude and oxidative stress: antioxidant nutrients", 2002, vol. 180, p. 107-119, Toxicology (13 pages).
Finaud et al., "Oxidative Stress: Relationship with Exercise and Training", 2006, vol. 36, No. 4, p. 327-358, Sports Medicine (33 pages).
Frucht, "Novel Israeli treatment zaps tumors using light and pigment", Dec. 5, 2004, ISRAEL21c, obtained from https://www.israel21c.org/novel-israeli-treatment-zaps-tumors-using-light-and-pigment/ (3 pages).
Greger, "How to Regenerate Coenzyme Q10 (CoQ10) Naturally", YouTube, Apr. 4, 2016, vol. 29, https://nutritionfacts.org/video/how-to-regenerate-coenzyme-q10-coq10-naturally/ (3 pages).
Guan et al., "Effects of Dietary Supplements on Space Radiation-Induced Oxidative Stress in Sprague-Dawley Rats", 2004, vol. 162, No. 5, p. 572-579, Radiation Research (9 pages).
Kennedy et al., "Biological countermeasures in space radiation health", 2003, vol. 16, No. 2, Gravitational and Space Biology Bulletin (8 pages).
Kennedy et al., "Countermeasures against space radiation induced oxidative stress in mice", Mar. 27, 2007, vol. 46, p. 201-203, Radiation and Environmental Biophysics (3 pages).
"LED Light Therapy", Natural Health Productions Inc., Aug. 11, 2017, http://www.mylighttherapy.com/led-light-therapy.html (9 pages).
Misra et al., "Oxidative stress and ischemic myocardial syndromes", Oct. 1, 2009, vol. 15, No. 10, p. RA209-RA219, Medical Science Monitor (11 pages).
Okunieff et al., "Antioxidants reduce consequences of radiation exposure", 2008, vol. 614, p. 165-178, Advances in Experimental Medicine and Biology (12 pages).
Qu et al., "Dietary Chlorophyll Metabolites Catalyze the Photoreduction of Plasma Ubiquinone", 2013, vol. 89, p. 310-313, Photochemistry and Photobiology (5 pages including abstract).
Sokolovic et al., "Melatonin Reduces Oxidative Stress Induce by Chronic Exposure of Microwave Radiation from Mobile Phones in Rat Brain", 2008, vol. 49, p. 579-586, Journal of Radiation Research (8 pages).
Traber et al., "Diet-derived and topically applied tocotrienols accumulate in skin and protect the tissue against ultraviolet light-induced oxidative stress", 1997, vol. 6, No. 1, p. 63-67, Asia Pacific Journal of Clinical Nutrition (5 pages).
Wambi et al., "Dietary Antioxidants Protect Hematopoietic Cells and Improve Animal Survival after Total-Body Irradiation", Apr. 2008, vol. 169, No. 4, p. 384-396, Radiation Research (25 pages).
Zhang et al., "Sequestration of ubiquitous dietary derived pigments enables mitochondrial light sensing", Oct. 12, 2016, vol. 6, No. 34320, Scientific Reports, Nature (13 pages).

* cited by examiner

*Primary Examiner* — Amanda K Hulbert
(74) *Attorney, Agent, or Firm* — Donald E. Hasse; Hasse & Nesbitt LLC

(57) ABSTRACT

Methods of treating a human subject exposed to radiation in space. The methods include the steps of administering to the subject in space a chlorophyll composition sufficient to provide at least about 0.15 µM of chlorophyll or its metabolites to the subject's bloodstream, and then exposing the subject in space to light having a wavelength of about 620 nm to about 760 nm and an intensity of about 5 W/m² to about 1000 W/m² for at least about 5 minutes. Methods for estimating the level of ubiquinol in the bloodstream of a subject having chlorophyll or chlorophyll metabolite in the bloodstream, which may be after treatment by the above methods, include the steps of exposing the subject's skin to light to induce fluorescence of the chlorophyll or chlorophyll metabolite, measuring the level of fluorescing chlorophyll or chlorophyll metabolite in the bloodstream using fluorescence spectroscopy, and correlating the level of fluorescing chlorophyll or chlorophyll metabolite to the level of ubiquinol using a predetermined scaling factor.

12 Claims, No Drawings

METHOD OF TREATING SUBJECT EXPOSED TO RADIATION IN SPACE

CROSS-REFERENCE TO RELATED APPLICATIONS

This application claims the benefit of U.S. Provisional Application No. 62/584,971, filed on Nov. 13, 2017, the disclosure of which is incorporated by reference in its entirety.

FIELD OF THE INVENTION

The invention relates to methods useful for treating a human subject exposed to high levels of radiation in space. More specifically, the invention relates to methods of treating a subject exposed to repeated or prolonged high levels of radiation in space to reduce the risk of, and ameliorate harmful effects from, such radiation.

BACKGROUND OF THE INVENTION

The radiation environment in space continuously induces high levels of oxidative stress in the human body, posing a significant hurdle for long term residence or travel outside the protection offered by Earth's atmosphere and magnetosphere. For perspective, the maximum allowed annual dosage for radiation workers in the US is 50 mS (millisievert). A six month stay on the International Space Station may expose an astronaut to a radiation dosage of 22 mS-52.5 mS, an average daily dosage of about 0.204 mS/day. The Apollo missions to the Moon lasted 8-14 days and resulted in an average dose rate of about 0.47 mS/day. An extended lunar mission of 180 days may expose an astronaut to a total dosage of about 170 mS, an average daily dosage of about 0.944 mS/day. The shortest currently-feasible mission to Mars of 600 days may expose an astronaut to a total dosage of 1,030 mS, an average daily dose of about 1.717 mS/day. A more realistic Mars mission of 1,000 days may result in a total dosage of about 1,500 mS, assuming that when on the Martian surface one is partially shielded by the mass of Mars at nighttime.

Oxidative stress can lead to muscle fatigue and an increased risk for cataracts, macular degeneration, cardiovascular disease and many forms of cancer, as well as other chronic diseases. Astronauts currently take dietary supplements of antioxidants, but these have shown limited efficacy in reducing levels of oxidative stress. One approach to solving this problem involves the addition of shielding material to manned spacecraft. However, the additional mass and volume of the shielding material results in unattractive engineering tradeoffs in spacecraft or habitat design.

Developing biological countermeasures for radiation injury is very challenging. Clinical research shows downstream biological effects from radiation damage are variable, based upon host factors, dose location, magnitude and rate, as well as the presence or absence of countermeasures.

U. S. Patent Publication 2013/0224281 A1 discloses radiation-oxidative exposure treatment compositions that include a mixture of micronutrient multivitamin and trace elements, antioxidants and chemopreventative agents, and optionally a mixture of fatty acids. Methods of treating a subject exposed to a radiation source or oxidative stress include administering a daily dose of the composition such that harmful effects induced by the radiation or oxidative stress are said to be ameliorated.

However, there is a continuing need for an effective method to protect humans from the harmful effects due to repeated or prolonged exposure to high levels of radiation in space.

SUMMARY OF THE INVENTION

The present invention relates to a method of treating a human subject exposed to radiation in space, the method comprising the steps of: (1) administering to the subject in space a chlorophyll composition sufficient to provide at least about 0.15 µM (micromoles/liter), of chlorophyll or its metabolites to the subject's bloodstream, and (2) then exposing the subject in space to light having a wavelength of about 620 nm to about 760 nm and an intensity of about 5 W/m$^2$ to about 1000 W/m$^2$ for at least about 5 minutes.

In one embodiment, the invention relates to a method of treating a human subject exposed to radiation in space, the method comprising the steps of: (1) administering to the subject in space a chlorophyll composition sufficient to provide at least about 1.0 µM of chlorophyll or its metabolites to the subject's bloodstream, and (2) then exposing the subject in space to light having a wavelength of about 620 nm to about 760 nm and an intensity of about 5 W/m$^2$ to about 300 W/m$^2$ for at least about 20 minutes, where the steps (1) and (2) occur on at least a daily basis during the period of exposure to radiation in space.

In another embodiment, the invention relates to a method for estimating the level of ubiquinol in the bloodstream of a human subject having chlorophyll or chlorophyll metabolite in the bloodstream, comprising the steps of: (a) exposing the subject to light to induce fluorescence of the chlorophyll or chlorophyll metabolite, (b) measuring the level of fluorescing chlorophyll or chlorophyll metabolite in the bloodstream using fluorescence spectroscopy, and (c) correlating the level of fluorescing chlorophyll or chlorophyll metabolite to the level of ubiquinol using a predetermined scaling factor.

DETAILED DESCRIPTION OF THE INVENTION

The specification and appended claims refer to particular features and method steps of the invention. The invention includes all combinations and uses of features and steps described herein. The invention is not limited to or by the description of embodiments or examples in the specification, and the terminology used for describing particular embodiments and examples does not limit the scope or breadth of the invention.

As used herein, the term "space" refers to being outside the limits of the Earth's atmosphere. While there is no firm boundary where space begins, the Kámán line at an altitude of 100 km (about 62 miles) above sea level is often used to designate the start of outer space. Thus, as used herein, "space" includes being on or in a vehicle, station or planetary body, including a planet, moon or asteroid, at an altitude of 100 km or greater above the sea level of the Earth.

As used herein, the term "chlorophyll composition" includes food compositions, dietary supplements or ingredients, and therapeutic compositions that provide chlorophyll in any suitable form, including chlorophyll a, b, c1, c2, c3, d and f, chlorophyll metabolites, and/or synthetic modifications of chlorophyll and its metabolites, to the subject's bloodstream. Chlorophyll metabolites useful herein include, but are not limited to, those described in "Qu, J. et al., Dietary Chlorophyll Metabolites Catalyze the Photoreduction of Plasma Ubiquinone, Photochemistry and Photobiology, 89: 310-313 (2013), incorporated herein by reference. A variety of chlorophyll metabolites, such as chlorophyllide-a, pheophytin-a, pheophorbide-a, methyl pheophorbide-a, 10-OH-pheophorbide-a, 10-OH-methyl pheophorbide-a, pyropheophorbide-a and methyl pyropheophorbide, may be present in the blood. The above metabolites may be formed from chlorophyll by chemistry that normally takes place in the body. Chlorophyll compositions herein also include synthetic modifications of chlorophyll and its metabolites that provide additional or different properties, for example, that extend the half-life, bioavailability or reactivity of chlorophyll compounds and metabolites in the bloodstream.

The present invention provides a method of treating a human subject exposed to radiation in space. The method comprises the steps of: (1) administering to the subject a chlorophyll composition sufficient to provide at least about 0.15 µM of chlorophyll or its metabolites to the subject's bloodstream, and (2) then exposing the subject to light having a wavelength of about 620 nm to about 760 nm and an intensity of about 5 W/m$^2$ to about 1000 W/m$^2$ for at least about 5 minutes. The method provides a biological countermeasure to reduce the risk of, and ameliorate harmful effects from, exposure to repeated or prolonged high levels of radiation in space.

Ubiquinol, the fully reduced form of coenzyme Q10, is an antioxidant that the body manufactures. When ubiquinol interacts with free radicals, it is oxidized into ubiquinone which is stable and does not propagate an oxidative chain reaction. The benefit of this is that a free radical "damages" ubiquinol instead of biological tissue, such as an enzyme, cell wall, RNA, or DNA. The body manufactures a series of enzymes which can regenerate ubiquinol from ubiquinone, thus recharging the body's antioxidant buffer. However, the rate of this enzymatic recharging is limited and not sufficient to overcome an environment of sustained oxidative stress, such as during prolonged or repeated exposure to high levels of radiation encountered during space travel or habitation in space.

Chlorophyll is found in green leafy vegetables, such as spinach, kale, cabbage, garden cress, bok Choy, broccoli, and brussels sprouts. Chlorophyll is an organic molecule sensitive to blue and red wavelengths of light that excels in converting electromagnetic energy into chemical potential energy. When humans consume chlorophyll-rich foods, chlorophyll and chlorophyll metabolites are absorbed into and circulate throughout the bloodstream. Red light from an external source can penetrate into the body in sufficient quantity to activate the chlorophyll and chlorophyll metabolites circulating in the bloodstream. In their activated state, these chlorophyll compounds catalyze the regeneration of ubiquinol from ubiquinone and provide a second avenue for recharging one of the body's primary endogenous antioxidants at a rate significantly higher than baseload metabolism can achieve. The invention thus provides an effective method for treating a subject exposed to repeated or prolonged high levels of radiation in space to reduce the risk of, and ameliorate harmful effects from, the radiation. The invention provides such benefits at a low cost and with more attractive engineering trade-offs compared to increased spacecraft or habitat shielding material thickness and mass. For example, every gram of payload landed on the surface of Mars may require about 110 grams of fuel and oxidizer to get it there, which themselves require larger, heavier fuel tanks and engines with more thrust capacity. Such high diminishing returns necessitate strict rationing of mass in spacecraft design. Thus, the invention provides a potentially high ratio of efficacy to cost in manned spaceflight.

The chlorophyll composition is administered to the subject, via diet or otherwise while in space, at a level sufficient to provide at least about 0.15 µM, typically at least about 0.25 µM, more typically at least about 0.5 µM, for example, at least about 1 µM, 1.5 µM, 2 µM, or 2.5 µM, of chlorophyll or its metabolites to the subject's bloodstream. The chlorophyll composition may be administered to the subject as a one-time event or relatively continuously, intermittently, or at intervals of time, typically at least on a daily basis, at a level sufficient to provide or maintain these concentrations in the subject's bloodstream. Lower levels of chlorophyll or its metabolites within the above ranges may be desirable when the subject is exposed to relatively constant, background radiation levels in space, and/or when the subject is maintaining a relatively constant level of chlorophyll or its metabolites in the bloodstream. The higher levels of chlorophyll or its metabolites may be desirable when the subject is exposed to periodic higher levels of radiation, and/or when the subject's diet varies the level of chlorophyll or its metabolites in the bloodstream.

In one embodiment, the chlorophyll composition may be formulated as a therapeutic composition provided in any acceptable dosage form, including capsules, tablets, lozenges, troches, hard candies, powders, sprays, elixirs, syrups, suspensions or solutions, and topical compositions, such as disclosed in U.S. Pat. No. 7,435,725, incorporated herein by reference. Such dosage forms may be conveniently taken before, during or between meals. In another example, the chlorophyll composition may be provided as a suspension or solution administered through an IV or feeding tube. The chlorophyll composition may be provided in the form of chlorophyllin and/or its salts, which may be administered to a subject in amounts that provide a daily dosage between about 20 mg and about 500 mg, typically about 40 mg to about 400 mg, more typically about 60 mg to about 300 mg. Since chlorophyllin and its salts are water soluble, they may be better suited than other compositions to administration by injection or through an IV.

After administration of the chlorophyll composition, the subject is exposed while in space to light having a wavelength of about 620 nm to about 760 nm and an intensity of about 5 W/m$^2$ to about 1000 W/m$^2$ for at least about 5 minutes. Typically, as much of the subject's skin as practical is exposed to the light. The wavelength of the light, light intensity, the length of time of the light exposure, and the timing of the light exposure after the administration or consumption of the chlorophyll composition, can all be incrementally varied without materially changing the invention. The exposure of the subject to light may be a one-time event or relatively continuously, intermittently, or at intervals of time, typically at least on a daily basis. As the intensity of the light increases within the above range, the duration of light exposure and/or the surface area of the subject's skin exposed to the light may be decreased. Conversely, if the duration of light exposure and/or the surface area of the subject's skin exposed to the light is increased, the intensity of the light may be decreased.

The wavelength of the light typically is in the range of about 620 nm to about 700 nm, more typically about 620 nm to about 680 nm, even more typically about 630 nm to about 670 nm, for example, about 635 nm, 645 nm, 660 nm, or 695 nm. The light may be provided in a narrow wavelength range that is optimized for the particular conditions, or the light may be in a broader wavelength range so long as sufficient light in the specified range is provided.

The intensity of the light typically is at least about 5 W/m$^2$, more typically at least about 10, 15 or 20 W/m$^2$. The intensity of the light typically is about 5 W/m² to about 500 W/m², more typically about 5 W/m² to about 400 W/m², and even more typically about 5 W/m² to about 300 W/m², for example, about 10 W/m² to about 200 W/m². In one embodiment, the target light intensity is about 180 W/m², about that of the red wavelengths of sunlight. The duration of exposure to the light in step (2) is typically at least about 10 minutes, more typically at least about 20 minutes, even more typically at least about 30 minutes, for example, at least about 1, 2 or 4 hours. The duration of exposure does not have to be continuous. For example, a 2-hour exposure may be one hour in the morning and one hour in the afternoon or evening. In some embodiments, longer exposure times may be desirable, for example, at least about 6, 8, 10, 12, 15, 18 or 24 hours.

In some embodiments, the light exposure in step (2) typically occurs within a period of about 1 hour to about 10 hours after administering the chlorophyll composition in step (1), more typically within a period of about 1 hour to about 8 hours after step (1), for example, within a period of about 1.5 hours to about 6 hours after step (1). The timing of the light exposure in step (2) may vary based upon the method of delivery of the chlorophyll composition. For example, it typically takes about 15 minutes for a stand-alone liquid to leave the stomach and enter the small intestine where absorption occurs. If the chlorophyll composition is a solid food or is mixed with solid food, it could take about 2 hours or more to leave the stomach and enter the small intestine where absorption occurs. It may take another 2 hours or more for the small intestine to absorb enough of the chlorophyll composition to provide at least about 0.15 µM of chlorophyll or its metabolites to the bloodstream. If the chlorophyll composition is a liquid that is injected intravenously, it may take only minutes to achieve the desired concentration of chlorophyll or its metabolites in the bloodstream. In such embodiments, the light exposure in step (2) typically occurs within about 1 hour after administering the chlorophyll composition in step (1), more typically within about 30 minutes after step (1), for example, within about 15 minutes after step (1). Since chlorophyll is lipid-soluble, ingestion with lipids may increase bioavailability of the chlorophyll or its metabolites in the subject's bloodstream.

In one embodiment, the subject is exposed to light having a wavelength of about 620 nm to about 700 nm and an intensity of about 5 W/m² to about 500 W/m² for at least about 10 minutes. Typically, the subject is exposed to light having a wavelength of about 630 nm to about 670 nm and an intensity of about 5 W/m² to about 300 W/m² for at least about 20 minutes, and typically at least about 30 minutes or 1 hour. In another embodiment, the above treatment steps (1) and (2) occur on at least a daily basis and begin at least 2 days before exposure to radiation in space. In yet another embodiment, the treatment steps (1) and (2) occur on at least a daily basis during the period of exposure to radiation in space. The treatment steps (1) and (2) typically occur at least twice a day during the period of exposure to radiation in space.

In some embodiments, it may be desirable to maintain the lower levels, within the above ranges, of chlorophyll or its metabolites in the bloodstream when the subject is exposed to a relatively constant, low intensity light. In some embodiments, it may be desirable to maintain a relatively constant level or low level of chlorophyll or its metabolites in the bloodstream when the subject is exposed to an environment that provides longer exposure to the light, or a relatively constant background light, having an intensity at the lower end of the specified range. In such low intensity light conditions, the duration of light exposure and/or the surface area of the subject's skin exposed to the light may be increased to provide the desired level of benefits. For example, the subject may be exposed to light having the specified wavelength and an intensity of about 5 W/m² to about 50 W/m², e.g., about 5 W/m² to about 35 W/m², or about 5 W/m² to about 25 W/m², or about 5 or 10 W/m², for at least about 4 hours, or at least about 6, 8, 10, 12, 18 or 24 hours. The low intensity light may be provided in a special room, for example an exercise or sleeping room, or incorporated into a personal or portable electronic device or medical device, such as an LED-imbedded wristband that is worn in close contact with the high blood flow in the wrist of the subject, or a neck collar with an LED in close proximity to the carotid arteries, or an LED-imbedded vest worn across the torso. Another benefit is that the user of such a low intensity light would have less need to dissipate excess heat away from the body. In reduced gravity environments, the magnitude of thermal convection is reduced so heat dissipation away from the skin is slowed, possibly resulting in astronaut discomfort. When using such a low intensity light, one should select optimum light wavelengths to obtain the most efficient use of the light. The wavelength of light, light intensity, the length of time of the light exposure, and the timing of the light exposure after the administration or consumption of the chlorophyll composition may all be selected to optimize the benefits provided by the invention based on the expected radiation exposure levels. In another embodiment, the light may comprise essentially only infrared wavelengths so as not to be visually disruptive to humans, such as during sleep.

In one example, an astronaut's diet in space provides a relatively constant level of at least about 0.15 µM, e.g., about 0.5 µM, of chlorophyll or its metabolites in the bloodstream. The astronaut is exposed to light having a wavelength of about 630 nm to about 670 nm and an intensity of about 10 W/m² for about 12 hours during the day by wearing an LED-imbedded wristband having a surface area of about 45 cm². In another example, an astronaut's diet provides a relatively constant level of at least about 0.15 µM, e.g., about 1 or 2 µM, of chlorophyll or its metabolites in the bloodstream. The astronaut wears athletic clothing that expose about 1.5 m² of skin while exercising for about 1 hour in an LED-lit room in which the light has a wavelength of about 630 nm to about 710 nm and an intensity of about 180 W/m².

In another embodiment, the invention provides a medical regimen for an astronaut exposed to repeated or prolonged high levels of radiation in space that can substantially enhance the mean antioxidant level within the astronaut's body and provide meaningful reduction in radiation induced health problems. The regiment may comprise dietary intake of a chlorophyll composition in the form of dark leafy greens, edible algae, or other suitable sources. After the chlorophyll or its metabolites are present in the bloodstream (e.g., 1-10 hours after consumption of a food, dietary supplement, or therapeutic composition providing chlorophyll or chlorophyll-metabolites to the bloodstream), the application of light having a wavelength of about 620 nm to about 760 nm to as much skin surface as possible activates the chlorophyll compounds within the bloodstream and catalyzes the regeneration of ubiquinol. The light intensity should be about 5 W/m² to about 1000 W/m², and the light exposure should be at least about 5 minutes. Longer exposure times may increase the benefit provided and pose little or no risk to the subject, provide the light intensity is adjusted to balance the exposure time. It may be desirable for the light exposure to occur while the astronaut is exercising because the increased blood flow provides increased mixing of the activated chlorophyll compounds and ubiquinone. During exercise, the blood is also brought closer to the skin surface, which increases the amount of light reaching the chlorophyll compounds in the bloodstream. The above steps may be repeated on a daily basis, or twice per day, e.g., once in morning and once in the evening, or even more frequently to provide a higher and more constant level of activated chlorophyll compounds in the bloodstream, and thus a higher and more constant level of the ubiquinol antioxidant in the bloodstream.

The light generation and delivery during step (2) of the invention may be provided by various methods. For example, the light may be provided by a tanning bed, by LEDs strapped onto the body or imbedded in clothing, in a light room with reflective walls, via a spotlight or sun lamp, etc. The light is typically provided by an efficient and rechargeable light source, such as an LED light source, which may be included in a portable device designed to be worn by the subject.

In some embodiments, it is particularly desirable that the subject have a sufficient level of Vitamin C in the bloodstream when practicing the present invention. While not intending to be limited by theory, it is believed that Vitamin C may play a role in catalyzing the regeneration of ubiquinol from ubiquinone. Vitamin C is typically already present in a person's diet. However, if not present at a sufficient level in the bloodstream, it may be administered to the subject to provide at least about 70 mg, typically at least about 100 mg, more typically at least about 125 mg, and even more typically at least about 150 mg, of Vitamin C per day in the diet. Ascorbic acid is a source of Vitamin C. Water-soluble salts of ascorbic acid, such as sodium ascorbate, are also suitable.

In some embodiments, it may be desirable to administer to the subject a dietary supplement comprising at least about 25 mg, typically at least about 50 mg, up to about 400 mg, per day of ubiquinol or ubiquinone (coenzyme Q10) to enhance the benefits provided by the present invention.

It may be desirable to add a source of UV wavelengths into the light provided in step (2), or separately before, during or after the light exposure provided in step (2), as a means of simultaneously or separately boosting vitamin D production in the subject. Astronauts currently take vitamin D supplements, but typically still fail to achieve desired serum levels of vitamin D. Thus, the method of the invention may further comprise the step of exposing the subject to ultraviolet light having a wavelength of about 270 nm to about 320 nm for at least about 5 minutes, typically at least about 15 minutes, more typically at least about 20 minutes.

Astronauts almost universally develop warped sleep cycles in space for reasons not fully understood. It is known that red light stimulates the production of melatonin and affects cortisol levels as well. The exposure to red light within the above wavelength ranges may be timed to help regulate the subject's sleep cycle and circadian rhythm. Thus, the method of the invention may further comprise the step of timing the treatment step (2) to help regulate the subject's sleep cycle and circadian rhythm.

It may be desirable to estimate the level of ubiquinol in the bloodstream of a subject based on the level of chlorophyll or chlorophyll metabolite in the bloodstream, in real time without drawing blood samples to directly measure the ubiquinol level. Since chlorophyll fluoresces at unique wavelengths, for example, it emits at about 680 nm to about 750 nm (e.g., 685 or 730 nm) when exposed to light having a wavelength of about 335 nm to about 360 nm (e.g., 355 nm) or about 457 nm, and the body is semi-transparent to this fluoresced wavelength, one can measure blood chlorophyll levels in real time using fluorescence spectroscopy and a sensitive photometer and correlate this to ubiquinol levels via a scaling factor determined by experimental observation. Thus, in another embodiment, the invention provides a method for estimating the level of ubiquinol in the bloodstream of a human subject having chlorophyll or chlorophyll metabolite in the bloodstream, comprising the steps of: (a) exposing the subject's skin to light to induce fluorescence of the chlorophyll or chlorophyll metabolite, (b) measuring the level of fluorescing chlorophyll or chlorophyll metabolite in the bloodstream using fluorescence spectroscopy, and (c) correlating the level of fluorescing chlorophyll or chlorophyll metabolite to the level of ubiquinol using a predetermined scaling factor. The scaling factor is experimentally determined by measuring ubiquinol blood levels before and after exposure to known quantities of chlorophyll or chlorophyll metabolite and light having a wavelength, intensity and duration, as described above, on a control group of representative subjects. The method of estimating the level of ubiquinol in the bloodstream may be accomplished without drawing a blood sample from the subject. The level of ubiquinol in the bloodstream of the subject can then be adjusted upward to a desired level by practicing treatment steps (1) and (2) above, and/or by adjusting the intake of the chlorophyll composition, the wavelength of the light, light intensity, time of light exposure, and time after consumption of the chlorophyll composition, as described above.

In another embodiment, the above method for estimating the level of ubiquinol in the bloodstream may be practiced after treating a subject exposed to radiation by the method comprising the steps of: (1) administering to the subject a chlorophyll composition sufficient to provide at least about 0.15 µM of chlorophyll or its metabolites to the subject's bloodstream, and (2) then exposing the subject to light having a wavelength of about 620 nm to about 760 nm and an intensity of about 5 W/m$^2$ to about 1000 W/m$^2$ for at least about 5 minutes.

In another embodiment, the fluorescence data and/or predicted ubiquinol level may be used to adjust the subject's chlorophyll composition ingestion and/or light exposure in real time to achieve a sufficient level of risk reduction or protection from radiation exposure in the subject's environment. This aspect of the invention may be particularly useful when the subject is exposed to changing radiation environments or is subjected to long term radiation exposure. Thus, the above method for estimating the level of ubiquinol in the bloodstream may be followed by the step of adjusting the level of ubiquinol in the bloodstream of the subject by: (1) administering to the subject a chlorophyll composition sufficient to provide at least about 0.15 µM of chlorophyll or its metabolites to the subject's bloodstream, and (2) then exposing the subject to light having a wavelength of about 620 nm to about 760 nm and an intensity of about 5 W/m$^2$ to about 1000 W/m$^2$ for at least about 5 minutes.

In another embodiment, the invention further comprises administering to the subject on at least a daily basis a dose of a radiation-oxidative exposure treatment composition comprising an effective amount of one or more micronutrient multivitamins, trace elements, antioxidants, chemopreventative agents, and fatty acids, and mixtures thereof, such as described in U. S. Patent Publications 2013/0224281 A1 and 2014/0023701 A1, both incorporated herein by reference. The radiation-oxidative exposure treatment composition typically comprises a mixture of the micronutrient multivitamin and trace elements, a mixture of antioxidants and chemopreventative agents, and optionally a mixture of fatty acids. Compositions comprising low levels of each of the most effective micronutrient multivitamins, trace elements, antioxidants, chemoprevention agents and optional fatty acids, provides a broad range of cellular protection and bioavailability without the toxicity usually associated with high single doses of particular vitamins, elements, antioxidants, chemoprevention agents, and lipids.

Micronutrient vitamins important for dietary requirement include Vitamins A, B1, B2, B3, B5, B6, B7, B9, B12, C, D, E and K, and coenzyme Q10. Some of these vitamins also have antioxidant properties. There may be more than one source for micronutrient vitamins. Vitamin A palmitate and beta-carotene, and combinations thereof, are sources of Vitamin A. Choline bitartrate is a source of choline. Ascorbic acid is a source of Vitamin C. Sodium ascorbate is also a source for Vitamin C. Cholecalciferol is a source of Vitamin D. D-alpha tocopheryl succinate and mixed tocopherols, and combinations thereof, are sources of Vitamin E. Natural and mixed carotenoids are good sources of Vitamin E. Phytonadione is a source of Vitamin K. Thiamine can originate from thiamine mononitrate, which provides Vitamin B1. Riboflavin is a source of Vitamin B2. Niacin can originate from inositol hexanicotinate, which provides Vitamin B3. Pyridoxine hydrochloride is a source of Vitamin B6. Folate provides Vitamin B9. Cyanocobalamin is a source of Vitamin B12. Biotin is a source of B7. Pantothenic acid can originate from d-calcium pantothenate, which provides Vitamin B5. Although no longer considered a Vitamin B complex on its own, many vitamin supplement formulations still include inositol for its general bioactivity. Inositol hexanicotinate is the niacin-esterified version of inositol. Inositol and inositol hexanicotinate, and combinations thereof, can provide inositol.

Various trace elements important for the dietary requirements include calcium, iodine, magnesium, zinc, selenium, copper, manganese, chromium, molybdenum, potassium, boron and vanadium. There may be more than one source for trace elements. Calcium carbonate and dicalcium phosphate, and combinations of the two, are sources of calcium. Magnesium oxide and chelate, and combinations of the two, are sources of magnesium. Zinc chelate [monomethionine], zinc oxide and zinc gluconate are sources of zinc. Zinc oxide provides the most concentrated form of elemental zinc. L-selenomethionine is a source of selenium. Copper amino acid chelate, copper oxide and copper gluconate are sources of copper. Manganese amino acid chelate is a source of manganese. Chromium polynicotinate is a source of chromium. Molybdenum amino acid chelate is a source of molybdenum. Potassium citrate is a source of potassium. Boron chelate is a source of boron. Vanadyl sulfate is a source of vanadium.

The antioxidant and chemopreventative agent mixture is a combination of botanical extracts, carotenoids, flavonoids, and other ancillary compounds, which can provide antioxidant activity and some measure of protection against oxidative stress. Antioxidant and chemopreventative agent mixtures contain non-essential natural antioxidants and chemopreventative agents, including rutin, quercetin, hesperidin, alpha lipoic acid (ALA), N-acetyl-L-cysteine (NAC), lutein, lycopene, astaxanthin, plant sterols, isoflavones, garlic, garlic extract, green tea extract, cruciferous vegetables and their extracts, fruit blends, and resveratrol. It may also contain other similar non-essential antioxidant ingredients that are botanical, nutritional, dietary, additive, or otherwise Generally Recognized as Safe (GRAS) and allowed within the applicable jurisdiction, and not already listed herein, such as glutathione, cumin, curcumin, turmeric, heat-treated turmeric, ginger, zingerone, zerumbone, rosemary, piperine, lemon balm, clove, acai, caffeine, L-ergothioneine, and sulforaphane, e.g., from broccoli or other cruciferous vegetables. Soy extract is a source for isoflavones. Bulb garlic is a source for garlic extract. Green tea leaf is a source for green tea extract and epigallocatech gallate. The green tea leaf extract is standardized to 95% polyphenols and 50% epigallocatech gallate (EGCG). Broccoli sprouts are a source for cruciferous vegetable extract. Strawberries, escobillo, blueberries, blackberries, cranberries, grapes, amla, lemons and pomegranates are sources for fruit blends.

Optionally, the radiation-oxidative exposure treatment compositions include a mixture comprising fatty acids, including omega-3 fatty acids. Fatty acids have a number of beneficial health effects. Eicosapentaenoic acid (EPA) and docosahexaenoic acid (DHA), classified as omega-3 fatty acids, are believed to have anti-inflammatory activity and are sometimes used as dietary supplements with inflammatory conditions, such as Crohn's disease and rheumatoid arthritis. Omega-3 fatty acids are needed for prostaglandins, which are hormone-like substances that regulate dilation of blood vessels, inflammatory responses, and other critical body processes. DHA and EPA are also believed essential for nerve and eye functions. DHA comprises about 60 percent of the z rod segments of photoreceptor cells that are used to see with by humans. Brain tissue has a substantial component of fat composed of DHA. It is believed that algae-derived omega-3 fatty acids, specifically, DHA and EPA, are useful in wet macular degeneration since these fatty acids help heal and support blood vessel walls. And since chlorophyll and at least some of its metabolites are fat soluble, having even a small amount of fatty acid lipids in the digestive track should boost absorption of chlorophyll and its metabolites.

Radiation-oxidative exposure treatment compositions comprising micronutrient vitamins, trace elements, non-essential natural antioxidants, chemoprevention agents and optionally fatty acids, may ameliorate harmful effects of radiation exposure. Treatment with such compositions may also ameliorate organ-specific late radiation injuries, which may include pulmonary fibrosis, renal failure, hepatic fibrosis and central nervous system damage, which can result in neuro-cognitive impairment. Treatment with such compositions can also ameliorate the acute effects of total-body irradiation.

The radiation-oxidative exposure treatment compositions may be useful for pre- or post-exposure treatment to radiation sources or sources of oxidative stress, or both, that impact a subject. Exposure to either or both of these damaging sources can induce life-shortening effects. Daily administration of the radiation-oxidative exposure treatment compositions can ameliorate these post-exposure life-shortening effects. The composition can be effective for subjects exposed to radiation in space.

The administration of the radiation-oxidative exposure treatment compositions can be self-introduced, for example, making oneself the subject of the daily administration of the treatment. Examples of self-introduction include orally consuming the composition with meals or as capsules, injecting oneself with a solution comprising the composition, and applying an ointment comprising the composition to one's skin. Examples of administration of the radiation-oxidative exposure treatment compositions to a subject not oneself include feeding a subject a foodstuff comprising the composition as part of a daily meal and injecting a subject with a solution comprising the composition. One of ordinary skill can device numerous methods of administering radiation-oxidative exposure treatment compositions to subjects to affect the proper daily dose. These can include time-release capsules, orally ingested liquids, intraperitoneal, intravenous, subcutaneous, sublingual, transcutaneous, intramuscular, and other well-understood forms.

The radiation-oxidative exposure treatment composition can be administered or introduced to a subject as a pure or refined material. Typically, the composition is dilution by blending with other materials for ingestion or injection, including foodstuffs (water, drinks, meals) edible solids, gels; palatable liquids and solutions; salines and fluids for intramuscular administration; and inert binding materials.

Oral consumption is one method of administration since digestion metabolizes many of the component mixtures, especially antioxidant compounds, into their active and protective forms. Oral consumption is also a comfortable and palatable delivery vehicle for introduction of the radiation-oxidative exposure treatment compositions. Forms of the radiation-oxidative exposure treatment composition for oral administration, either in pure or diluted form, include lacquered or coated tablets, unlacquered or uncoated tablets, caplets, hard capsules, liquid-filled capsules, hard gelatin capsule, hard vegetable-based capsule, elixir, soft-chew, lozenge, chewable bar, juice suspension, liquids, time-release formulations, and foodstuffs.

Where a range of values is provided, it is understood that each intervening value between the upper and lower limit of that range and any other stated or intervening value in that range is encompassed within the invention. The upper and lower limits of these smaller ranges may independently be included in the smaller ranges, and is also encompassed within the invention, subject to any specifically excluded limit in the stated range. Where the stated range includes one or both of the limits, ranges excluding either or both of those included limits are also included in the invention.

It should be apparent to those skilled in the art that modifications of the present invention besides those described are possible without departing from the inventive concepts. The inventive subject matter, therefore, is not restricted except as stated in the disclosure.

In interpreting the disclosure, all terms should be interpreted in the broadest possible manner consistent with the context. In particular, the terms "comprise" and "comprising" should be interpreted as referring to elements, components, or steps in a nonexclusive manner, indicating that the referenced elements, components, or steps may be present, or utilized, or combined with other elements, components, or steps that are not expressly referenced.

Where reference is made to a method comprising two or more defined steps, the steps can be carried out in any order or simultaneously (except where the context excludes that possibility), and the method can include one or more other steps which are carried out before any of the defined steps, between two of the defined steps, or after all the defined steps (except where the context excludes that possibility).

I claim:

1. A method of treating a human subject exposed to radiation in space, the method comprising the steps of:
   (1) administering to the subject in space a chlorophyll composition sufficient to provide at least 1.0 µM of chlorophyll or its metabolites to the subject's bloodstream, and
   (2) then exposing the subject in space to light having a wavelength of 620 nm to 760 nm and an intensity of 5 W/m$^2$ to 1000 W/m$^2$ for at least 5 minutes to activate the chlorophyll composition in the bloodstream and catalyze the regeneration of ubiquinol antioxidant in the subject to reduce the risk of and ameliorate harmful effects from exposure to radiation in space.

2. The method of claim 1 where the steps (1) and (2) occur on at least a daily basis during the period of exposure to radiation in space.

3. The method of claim 1 where the steps (1) and (2) occur at least twice a day during the period of exposure to radiation in space.

4. The method of claim 1 where the chlorophyll composition provides at least 2.5 µM of chlorophyll or its metabolites to the subject's bloodstream.

5. The method of claim 1 where the step (2) occurs within a period of 1 hour to 10 hours after the step (1).

6. The method of claim 1 where in step (2) the subject is exposed to light having a wavelength of 620 nm to 700 nm and an intensity of 5 W/m$^2$ to 500 W/m$^2$ for at least 10 minutes.

7. The method of claim 1 where in step (2) the subject is exposed to light having a wavelength of 630 nm to 670 nm and an intensity of 5 W/m$^2$ to 300 W/m$^2$ for at least 20 minutes.

8. The method of claim 1 where in step (2) the light is provided by an LED light source.

9. The method of claim 1 further comprising exposing the subject to ultraviolet light having a wavelength of 270 nm to 320 nm for at least 10 minutes.

10. The method of claim 1 where Vitamin C is present in the subject's bloodstream.

11. The method of claim 1 further comprising administering to the subject on at least a daily basis a radiation-oxidative exposure treatment composition comprising micronutrient multivitamins, trace elements, antioxidants, chemopreventative agents, and fatty acids, and mixtures thereof.

12. A method of treating a human subject exposed to radiation in space, the method comprising the steps of:
   (1) administering to the subject in space a chlorophyll composition sufficient to provide at least 1.0 µM of chlorophyll or its metabolites to the subject's bloodstream, and
   (2) then exposing the subject in space to light having a wavelength of 620 nm to 760 nm and an intensity of 5 W/m$^2$ to 300 W/m$^2$ for at least 20 minutes to activate the chlorophyll composition in the bloodstream and catalyze the regeneration of ubiquinol antioxidant in the subject to reduce the risk of and ameliorate harmful effects from exposure to radiation in space,
   where the steps (1) and (2) occur on at least a daily basis during the period of exposure to radiation in space.

* * * * *